United States Patent
Liu

(10) Patent No.: US 11,654,099 B2
(45) Date of Patent: *May 23, 2023

(54) PRODUCING A TOPICAL SOLUTION COMPOSITION

(71) Applicant: Shantel Medical Supply Corp., Arcadia, CA (US)

(72) Inventor: Kay Liu, San Marino, CA (US)

(73) Assignee: Shantel Medical Supply Corp., Arcadia, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 16/997,121

(22) Filed: Aug. 19, 2020

(65) Prior Publication Data

US 2021/0030662 A1  Feb. 4, 2021

Related U.S. Application Data

(63) Continuation of application No. 15/715,037, filed on Sep. 25, 2017, now Pat. No. 10,888,515, which is a continuation-in-part of application No. 15/685,687, filed on Aug. 24, 2017, now abandoned, which is a continuation of application No. 11/837,735, filed on Aug. 13, 2007, now Pat. No. 9,770,480.

(51) Int. Cl.
| | |
|---|---|
| *A61K 8/96* | (2006.01) |
| *A61K 8/67* | (2006.01) |
| *A61K 8/06* | (2006.01) |
| *A61Q 19/02* | (2006.01) |
| *A61K 8/34* | (2006.01) |
| *A61K 8/9789* | (2017.01) |

(52) U.S. Cl.
CPC .......... *A61K 8/96* (2013.01); *A61K 8/06* (2013.01); *A61K 8/347* (2013.01); *A61K 8/673* (2013.01); *A61K 8/678* (2013.01); *A61K 8/9789* (2017.08); *A61Q 19/02* (2013.01); *A61K 2800/85* (2013.01)

(58) Field of Classification Search
None
See application file for complete search history.

(56) References Cited

U.S. PATENT DOCUMENTS

| | | | |
|---|---|---|---|
| 5,989,596 A * | 11/1999 | Bresson-Rival | A61Q 5/02 424/711 |
| 6,124,364 A | 9/2000 | Breton et al. | |
| 6,238,678 B1 | 5/2001 | Oblong et al. | |
| 6,280,712 B1 | 8/2001 | Ansmann et al. | |
| 9,770,480 B2 | 9/2017 | Liu | |
| 10,888,515 B2 * | 1/2021 | Liu | A61K 8/06 |
| 2006/0078530 A1 | 4/2006 | Liu | |
| 2006/0153822 A1 * | 7/2006 | Bou | C12P 7/56 435/252.9 |
| 2007/0003644 A1 | 1/2007 | Randhava et al. | |
| 2007/0009455 A1 | 1/2007 | Kim et al. | |
| 2007/0122502 A1 * | 5/2007 | Logsdon | A61K 45/06 424/766 |
| 2009/0047372 A1 | 2/2009 | Miller | |

OTHER PUBLICATIONS

"The pH levels of Apple, Orange, Grape and Cranberry Fruit Juices" from https://healthyeating.sfgate.com/ph-levels-apple-orange-grape-cranberry-fruit-juices-12062.html—accessed Jun. 2022.*
"All You Need to Know About Xanthan Gum" (https://www.medicalnewstoday.com/articles/320272#what-is-xanthan-gum-used-for)—accessed Jun. 2022.*
"Portfolio Winery" website (https://web.archive.org/web/20060324003616/http://www.portfoliowinery.co- m/winery.html—internet archived version from Mar. 2006).
Burns, J et al., J. Agric. Food Chem. (2001); 49:5797-5808. Extraction of phenolics and changes in antioxidant activity of red wines during vinification.
MacNeil (The Wine Bible. Workman Publishing: New York, 2001, Print. Exerpt, pp. 30-35).
Wikipedia contributors. Magenta. Wikipedia, The Free Encyclopedia. Downloaded Sep. 15, 2013. Retrived from http://simple.wikipedia.org/wiki/Magenta, pp. 1-8.
Wikipedia: "Pinot noir". Downloaded from the world wide web on Aug. 15, 2010.

* cited by examiner

*Primary Examiner* — Susan Hoffman
(74) *Attorney, Agent, or Firm* — Alberto O. Amatong, Jr.; Amatong McCoy LLC

(57) ABSTRACT

The appearance of hyperpigmented lesions on human skin are reduced by applying a topical solution composition that includes a concentrated amount of resveratrol that has been extracted from red wine and is at a pH of between 2.5 and 5.5.

27 Claims, 3 Drawing Sheets

25 Tea, pre- and post-

PRODUCING A TOPICAL SOLUTION COMPOSITION

This present application is a Continuation Application of U.S. application Ser. No. 15/715,037, filed on Sep. 25, 2017, U.S. Pat. No. 10,888,515, which is a Continuation-in-Part of U.S. application Ser. No. 11/837,735, filed on Aug. 13, 2007, now U.S. Pat. No. 9,770,480, issued on Sep. 26, 2017, the entirety of which is incorporated herein by reference and made a part of the present disclosure. This application also claims priority to, as a Continuation in Part, U.S. patent application Ser. No. 15/685,687, filed on Aug. 24, 2017 (abandoned), the entirety of which is incorporated herein by reference and made a part of the present disclosure.

TECHNICAL FIELD

The present invention is generally related to a topical solution composition that revitalizes layers of the skin.

SUMMARY

The primary objective of the present invention is to produce a skin topical solution composition that revitalizes damaged skin. The production of the topical solution is accomplished by providing a grape extract and adding vitamins that are capable of increasing the pH and an aqueous solution with a carbomer base where the carbomer base acts as an emulsion stabilizer and where the grape extract is subjected to a fermentation and mixing process that yields the highest conversion of cis- and trans-piceid (a glucoside-analog of resveratrol) into cis- and trans-resveratrol.

The topical solution comprises a number of ingredients depending on if the desired final form of the topical solution is a gel or a cream. At a minimum the ingredients for the topical solution must include a grape extract, vitamins that are capable of increasing the pH and an aqueous solution with a carbomer base where the carbomer acts as an emulsion stabilizer and where the grape extract is subjected to a fermentation and mixing process that yields the highest conversion of cis- and trans-piceid (a glucoside-analog of resveratrol) into cis- and trans-resveratrol.

BACKGROUND

Figure 1:
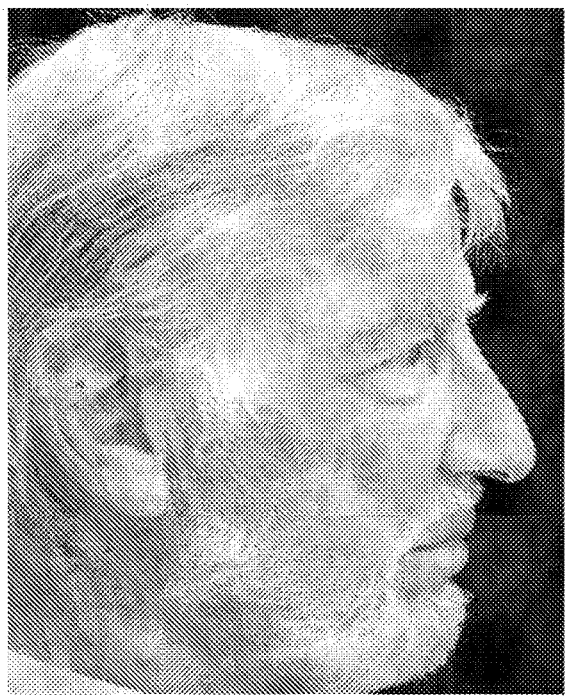
FIG. 1 Image of subject before and after using the skin lotion.
Figure 1:
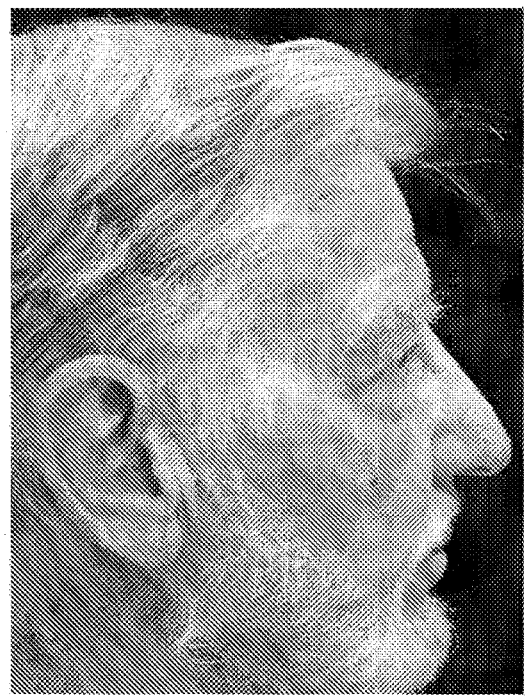

The present invention relates to revitalizing layers of the skin which have been damaged by the environment. More specifically, sunlight exposure and particularly ultraviolet radiation can cause a variety of skin changes and damages such as premature aging, and skin cancer. There are three main types of UV radiation, UVA, UVB, and UVC. UVC has the shortest wavelength. UVA on the other hand has the longest wavelength. However, as with any electromagnetic energy, the shortest wavelength is the most susceptible to obstruction while the longest wavelength is the least. UVC for example is almost completely blocked by the ozone layer in our atmosphere, while UVB penetrates the atmosphere relatively unobstructed and causes damage in the outer layer of the skin. UVB, however, does not penetrate glass. UVA, on the other hand, can penetrate glass and deeper into the skin to cause skin damage.

On a cellular level, UV radiation can cause collagen breakdown, creation of free radicals, interfere with DNA repair, and suppress the immune system's ability to survey and destroy cancerous cells. Of these damaging effects, perhaps the most significant is the creation of free radicals.

Oxygen molecules normally exist in stably bonded pairs. Free radicals are created when ionizing energy like UV radiation strikes a stable, paired oxygen molecule splitting its paired electron bonding, resulting in two single oxygen molecules. These two oxygen molecules each have one unpaired valence electron that is very reactive inside human tissues and cells. These free radical oxygen molecules react with organic molecules in the connective tissue and cells stealing electrons away from structures that require those electrons for stable bonds. This causes damage to enzymes, DNA's, collagen structures and cell wall stability and permeability. Damage to these cellular structures can cause for example. DNA mutations (that lead to cancerous behavior); suppression of enzymatic functions that regulate cellular signaling, apoptosis, immune functions, as well as, DNA repair.

One well known skin condition that occurs as a result of prolonged, cumulative effect of sun exposure is Actinic Keratosis, (AK's). AK's are by far the most common skin lesion with malignant potential on the skin. These lesions develop in a stepwise progression from subclinical skin changes to overt, invasive Squamous Cell Carcinoma, (SCC). If left untreated, these AK lesions have 1 per 1000 per year chance of becoming cancerous.

Clinically, AK's present with a range of characteristics. They can be barely perceptible to rough, elevated hyperkeratotic plagues several centimeters in diameter. The base may be light or dark, tan, pink, red, or a combination of these. Most typically though, they appear as multiple discrete lesions that are small crusty, scaly or crumbly bump or horn on an erythematous base.

Histologically, AK's share features with SCC. The histological characteristics are as follows: AK's are located in the epidermis and show hyperkeratosis with intermittent large parakeratotic nuclei and occasional mitotic figures; keratinocyte atypia along the basal layer spongiosis in the immediate suprabasalar layer; budding of the basal layer keratinocytes into the dermis; perivascular inflammation and solar elastosis.

Treatment of AK's typically consists of surgical destruction. The difficulty with surgical destruction is that it is difficult and impractical to treat a large area of the skin that has large number of lesions.

Hyperpigmentation is the condition of the appearance of excessive pigmented lesions on skin, which are often considered unsightly and undesirable. The causes of hyperpigmentation can vary but include excessive exposure to UVA and UVB radiation, detrimental environmental stress on skin through extended exposure, the side effects of light-based medical therapies on skin via laser or other devices (which is known as PIH or "Post-Inflammatory Hyperpigmentation"), hormonal changes to the human body that occur during or after pregnancy, as well as conditions such as melasma where pigmentation is a known side effect, or other physiological changes to the human body that can exhibit hyperpigmentation as a reaction to stress or inability to process toxicity within the body.

Historically hyperpigmentation has been one of the most difficult skin conditions to treat cosmetically, with traditional methods focusing on physical reduction of the pigment at the outermost layer of the skin (the stratum corneum) via a manual or chemical exfoliation process. The application of hydroquinone, a synthetic chemical originally compounded as a means of developing photographs, as a topically-applied medicine to reduce hyperpigmentation became a widely used method since the 1970s. However, hydroquinone has been found to have potentially significant effects if applied for too long of a period of time or if applied in higher concentrations. Specifically, there have been many documented cases of ocrhnosis where hyperpigmention is known to appear as a reaction to high does of hydroquinone and becomes intractable within skin. Because of safety considerations the health agencies of many nations have severely restricted or banned hydroquinone from use altogether, or at a minimum eliminated it as an OTC or "over the counter" medicine.

As a result, there is a need for a safer yet still effective means of reducing hyperpigmention through topical means. There have been several alternative compounds, both synthetic and from a botanical source, that have been applied to reduce hyperpigmentation, such as Vitamin C or Kojic Acid. However, these methods often have drawbacks in terms of difficulty to chemically stabilize, and have undesirable side effects on skin when applied.

DETAIL DESCRIPTION

The use of the present invention which, was further proven in studies performed by an independent research investigator at the Palo Alto Medical Foundation, greatly improves or completely resolves AK lesions. Furthermore, since the present invention consists of a topical solution that is topically applied it is not limited to impracticalities of treating large areas of the skin like surgical destruction.

Recently there has been significant interest in the medical and health industry generated about red wine. Red wine is known to have several biologically active compounds; most of them belong to a family known as polyphenols. Polyphenols are of great interest to the medical and health industry because of the potential benefits to human health. These compounds possess antioxidant, anti-inflammatory, and anticarcinogenic properties that are the focus of many current research investigations.

Polyphenols are a group of heterogeneous compounds with four main classes: flavonols, stilbenes, flavones, and phenolic acids. Such compounds include, for example, proanthocyanidins, quercitin, anthocyanins, and resveratrol and its glucoside analogs). Studies involving these four main classes suggest that of the polyphenols, resveratrol may the most effective in anticancer property.

Resveratrol exist as a cis-isomer and a trans-isomer. It falls under a class of polyphenols known as stilbenes. A glucoside analog of resveratrol is found naturally, to varying levels, in the skin of grapes in its isomeric forms called cis- and trans-piceid.

In the past, it was not known how to produce a grape extract to include in a topical solution where the grape extract was not damaged in the production process. Also, it was not known how to produce a grape extract that yields high levels of resveratrol. Finally due to fact that red wine and red wine's extract naturally has an extremely low pH (between 1.0 and 2.0) it was not known how to produce a topical solution that would not inflame or burn the skin.

In the present invention the grape extract is mixed by using a cold process which does not damage the grape extract, parameters in the fermentation process are heavily controlled to maintain a specific rage that yields high levels of resveratrol and certain ingredients are used in the production process that increases the natural pH level of red wine thereby allowing one to produce a topical solution with an acceptable pH and with the highest quantity of active polyphenols.

The topical solution composition of the present invention includes a grape extract which is produced predominantly from grapes that are rich in magenta color. We have found that grapes that are rich in magenta color yield the highest amount of resveratrol due to the high tannin content of the grapes' skin. We have also found that certain vintages like Merlot and Cabernet yield the highest form of resteratrol content because their vintage process includes more parts of the grapes' skin. Furthermore, there is a well known method of testing, growing and producing grapes with high levels of resveratrol.

Figure 3:
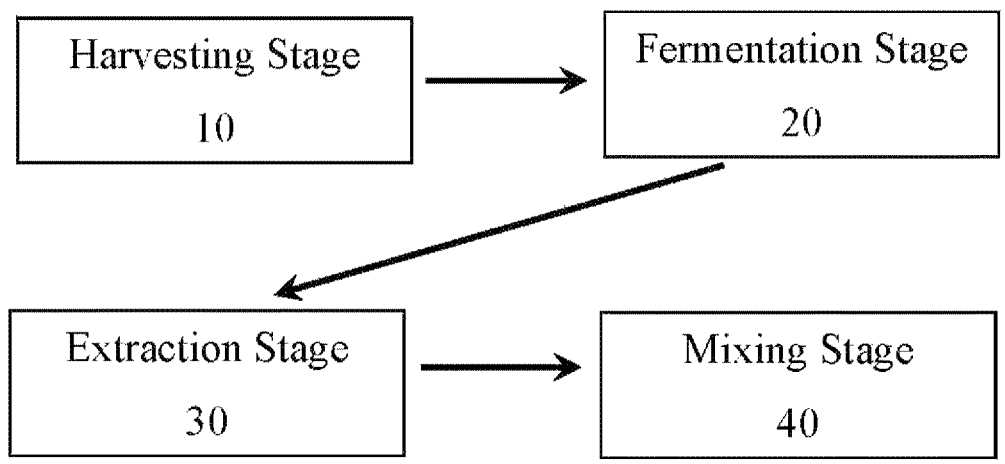
FIG. 3 is a simplified process flow diagram for developing a topical solution.
Figures 4A, 4B:
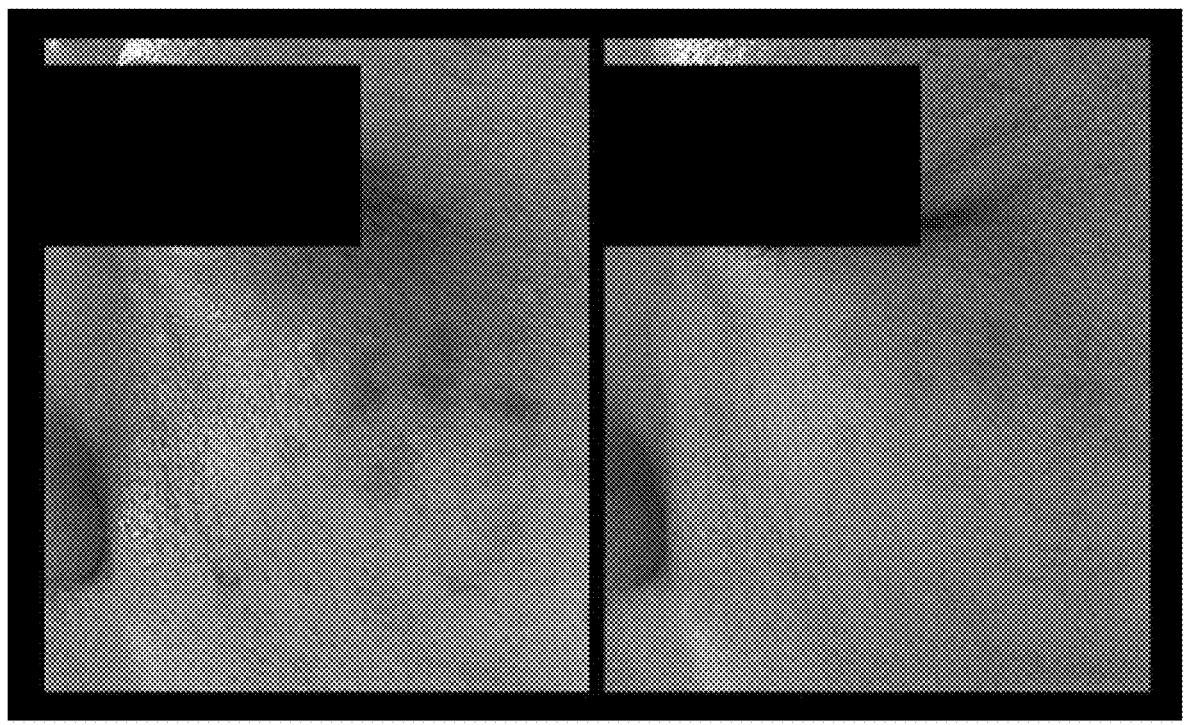
FIG. 4A is a photograph of the face of patient #1 on day 1 of the experiment described in Example 1, prior to any application of the topical solution composition, where lesions are visibly apparent on patient #1.
FIG. 4B is a photograph of the face of patient #1 on day 30 of the experiment described in Example 1, after the final application of the topical solution composition, where the number and/or size of the lesions that are visibly apparent on patient #1 have been reduced relative to FIG. 4A.
Figures 5A, 5B:
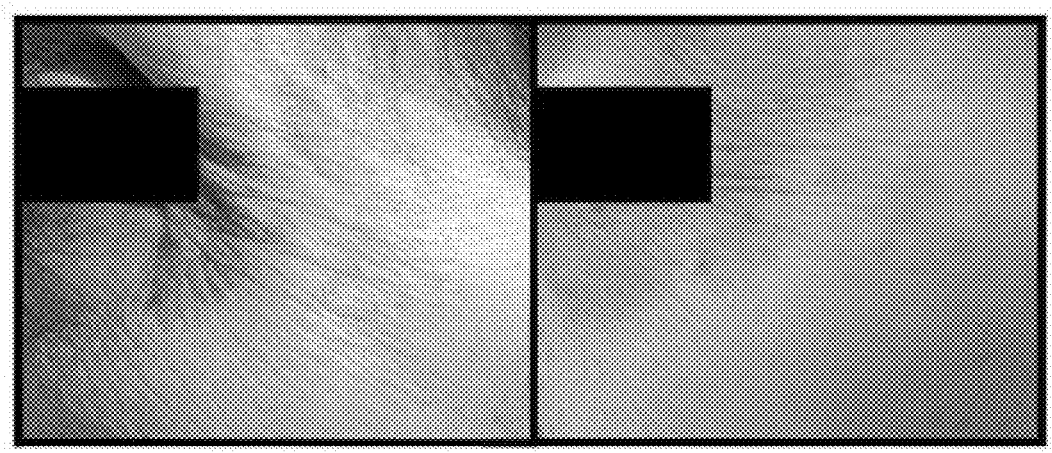
FIG. 5A is a photograph of the face of patient #2 on day 1 of the experiment described in Example 1, prior to any application of the topical solution composition, where lesions are visibly apparent on patient #2.
FIG. 5B is a photograph of the face of patient #2 on day 30 of the experiment described in Example 1, after the final application of the topical solution composition, where the number and/or size of the lesions that are visibly apparent on patient #2 have been reduced relative to FIG. 5A.

The process for developing the topical solution is referenced in the flow chart within FIG. 3 which starts with the harvesting stage (10) where grapes are harvested for their rich magenta color. The grapes are then subjected to a fermentation process named in FIG. 3 as the fermentation stage (20) which is a process in which an agent causes an organic substance to break down into simpler substances. The fermentation process used to produce the grape extract in the present invention includes the addition of yeast as the agent which causes the anaerobic breakdown of the sugar within the grape extract into alcohol. It is important that the fermentation parameters are strictly enforced. Too much fermentation yields an alcohol level that is more than two percent by volume. The increased level of alcohol above two percent by volume is a result that occurs when the fermentation process has begun to break down the Coumaroyl CoA molecule thereby not allowing it to yield the best reaction thereby yielding a long chain molecule. The preferred length of fermentation for the present invention depends on the temperature and humidity and the preferred range is between seven days at a temperature of ninety five degrees Fahrenheit and 80 percent humidity to forty five at a temperature of thirty five degrees Fahrenheit and 30 percent humidity. This range yields the highest conversion of cis- and trans-piceid (a glueoside-analog of resveratrol) into cis- and trans-resveratrol without oxidizing the polyphenols. After the fermentation process the grapes are then subjected to an extraction process which is performed in the extraction stage (30), where the water and ethanol content produced during the fermentation process is slowly removed leaving only the constituents of the grapes behind in a stable powder form.

This powder form of the grape extract is then subjected to the mixing stage (40) where depending if the designed outcome of the topical solution is a gel or cream various ingredients are added. The mixing process is particularly inventive due to the cold process mixing methods employed to mix the powder form of the grape extract into an aqueous solution with a carbomer base. Additional ingredients are then further added and mixed to increase the level of pH. The traditional mixing process uses heat to melt the ingredients thereby allowing the ingredients to adequately mix together. It is well known in the art of producing skin lotions to use high temperatures between 100 and 300 degrees Celsius in order to facilitate the melting and mixing of the ingredients. We have found that the use of high temperatures causes heat-oxidation in the grape extract. Heat oxidation occurs when elevated temperatures increase the activity of oxygen and serves as a catalyst by exothermic reactions for the formation of Radical Oxygen Species (ROS) from oxygen. When anti-oxidants such as resveratrol are exposed to heat-oxidation they bind with the ROS thereby decreasing the amount of resveratrol. In effect, heat-oxidization prematurely reduces or eliminates the anti-oxidant benefits of the grape extract.

In the present invention the mixing process of the grape extract is performed in room temperature between twenty to forty degrees Celsius thereby reducing any oxidation of the polyphenols caused by heat. This low temperature mixing process uses ingredients that are capable of being mixed without the need for increased temperatures.

This limits the types of ingredients one can use to in a skin lotion. We found that the following ingredients and their percentages are most contusive to mixing by use of a cold process when producing a topical solution using the present invention where the topical solution is in the form of a gel:

| Gel | |
|---|---|
| Ingredients: | Percentage |
| D.I. Water | 68.10 |
| RedWine Extract | 5.00 |
| *Aloe Barbensis* Extract | 4.00 |
| Cucumber Extract | 3.00 |
| Hylauronie Acid | 2.50 |
| Isoplene Glycol | 2.00 |
| Tocopherol Acetate | 2.00 |
| Chamomile Extract | 2.00 |
| Jojoba Oil | 2.00 |
| Hydrolyzed Milk Protein | 2.00 |
| Nettle (*Urtica Diolica*) Extract | 0.50 |
| Hydrolyzed Wheat Protein | 0.50 |
| Phytic Acid | 0.50 |
| Wheat Germ Oil | 0.50 |
| Horsetail Extract | 0.50 |
| *Centella Assistica* Extract | 0.50 |
| *Chlorella Vulgaris* Extract | 0.50 |
| Hydrolyzed Algin | 0.50 |
| Butylene Glycol | 0.50 |
| Naicinamide | 0.50 |
| Adensosine Triphosphate | 0.50 |
| D-Panthenol (Vitamin B5) | 0.50 |
| Carbomer | 0.20 |
| Xanthan Gum | 0.20 |
| Methylparaben | 0.20 |
| Butylparaben | 0.20 |
| Ethylparaben | 0.20 |
| Propylparaben | 0.20 |
| Triethanolamine | 0.20 |
| | 100.00 |

We also found that the following ingredients are most contusive to mixing by use of a cold process when producing a topical solution using the present invention where the topical solution is in the form of a cream:

| Cream | |
|---|---|
| Deionized Water | 62.6.0 |
| Grape extract | 6.00 |
| Isoprene Glycol | 5.00 |
| Squalane | 4.00 |
| *Santalum Album* Sandalwood Extract | 4.00 |
| *Phellodendron Amurense* Bank Extract, *Hordeum Distichon* (Barley) Extract, Polyglyceryl-2 Stearate | 2.00 |
| Ceteary Methicone (and) Dimethicone (and) Linleic Acid (and) *Glycine Soja* (soybean) Sterol (and) Phosopholipids | 2.00 |
| Dimethylopolsiloxane | 2.00 |
| *Chenesis* (Jojoba) Seed Oil | 2.00 |
| Tetrahexyldecyl Ascrobate | 3.00 |
| Tocopheryl Acetate (Vitamin E) | 3.00 |
| Cetyl Alcohol | 1.00 |
| Shea Butter | 1.00 |
| Phenoxyethanol (and) Methylparaben (and) Butylparaben (and) Ethylparaben (and) Propylparaben | 1.00 |
| Bees Wax | 0.50 |
| Cetearyl Glycoside | 0.50 |
| Xanthan Gum | 0.20 |
| Carbomer | 0.2 |
| Total | 100.00 |

It is important a topical lotion have a pH no less than 2.5 and no more than 8.0. If the pH of the topical solution composition is less than a pH of 2.5 or more than a pH of 8.0 the topical solution will burn the skin. The pH level of grape extract is between 1.0 and 2.0 which if applied would burn the skin. Therefore additional materials must be added to increase the pH level. In the present invention a form of vitamin E for example Tocopherol with a pH level between 4.0 and 7.0 is added to the topical solution and a form of vitamin B for example Panthenol with a pH level between 4.0 and 7.0 is added to the topical solution to increase the pH level. Either a form of vitamin E, a form of vitamin B or a form of vitamin E and vitamin B may be used to increase the level of pH of the grape extract. Furthermore, it is well known in the art that both vitamin E and vitamin B act to moisturize the skin thereby further complimenting the topical solution. Also, vitamin E and vitamin B are compatible with the cold process of the present invention.

The topical solution composition comprises: 0.1% to 50.0% of Grape extract of the total mixture and 0.100,% to 50.0% of an aqueous solution with a carbomer base of the total mixture, 0.1% to 50.0% of Vitamin B5, 0.1% to 50.0% of Vitamin E and, 0.1% to 50.0% water of the total mixture.

Figure 2:
FIG. 2 Image of subject before and after using the skin lotion.
Figure 2:

Results of our clinical study where subjects used the topical solution showed statistically significant improvements in AK's on skin. Each study subject was his/her own control. One side of the face was treated with the topical solution, while the other side was treated with a placebo gel which was simply the vehicle of the first topical gel without the skin lotion. The results show approximately 50%-85% improvement of AK's on the treatment side while the placebo side show little improvement or even progression of AK's. For example, in FIG. 1, the subject's treated side prior to treatment show 5 AK lesions and post-treatment show only 3 AK's. In FIG. 2, the treatment side of this subject showed 5 AK lesions and post-treatment shows only 1 AK lesion. These results were based on gross visual exam by the research investigator whose specialty is dermatology and confirmed by biopsy of skin lesions of the subjects on both sides of their faces.

The reduction of AK lesions after treatment with the skin lotion effectively makes it possible to treat a large area of skin affected with large number of AK's without significant side effects or discontinuation due to discomfort. Also, because our product has a low side effect profile, it can be used as a long-term maintenance product for patients with sun damaged skin to treat any subclinical cellular atypia that may not have been detected yet.

During the fermentation process resveratrol is produced from a Courraroyl CoA molecule with three Coumaroyl CoA molecules in three successive reduction reactions yielding a long chain molecule called tetraketide with a single benzene ring. Then that molecule is further process in acyclization process by either the resveratrol synthase or chalcone synthase to yield the final product of resveratrol or quercitin respectively. Our experience with various forms of red wine from a variety of grapes, and length of fermentation has resulted in a product that contains the highest quality of grape extract.

Various embodiments of the invention have been described. These and other embodiments are within the scope of the following claims.

Red Wine Composition for Inhibition of Pigmented Lesions on Human Skin

Certain aspects of the present disclosure include a red wine based composition suitable for use in the inhibition of pigmented lesions on human skin, to methods of making such a composition, and the methods of use of such a composition. Some such aspect includes a topical solution composition that exhibits the ability to lighten the appearance of human skin.

Without being bound by theory, it is believed that resveratrol, functioning as an anti-oxidant, has the effect of reducing melanin deposits on the surface of human skin. Resveratrol, a compound within red wine grape extract, has significant anti-inflammatory and anti-oxidant abilities. As the sole active ingredient, however, resveratrol is typically not directly applied to skin except in very small quantities, because resveratrol can cause skin irritation.

Without being bound by theory, it is believed that red wine grape extract, having a high concentration of resveratrol, has significant benefits for anti-oxidant activity upon human skin. For example, as disclosed in U.S. patent application Ser. No. 11/837,735 (the '735 application) and U.S. patent application Ser. No. 15/685,687 (the '687 application), grapes, fermented in accordance with the fermentation procedures described therein to develop the strength of the resveratrol without damaging its antioxidant abilities, are combined with vitamins in a carbomer base to create an effective topical composition to restore UV-radiation damaged skin. The abilities of such formulations were established by testing such formulations on patients with Actinic Keratosis (AK), a precursor condition to Squamous Cell Carcinoma (SCC) where lesions are visible on affected skin. The red wine-based topical solutions of such formulations exhibited the ability to reduce the appearance of AKs by an average of at least 75 percent within a two-month period of application. However, without being bound by theory, application of such formulations of red wine grape extract upon skin within a carbomer-based emulsifier does not appear to affect hyperpigmentation in a significant way, despite the relatively high anti-oxidant strength of such formulations.

Still, without being bound by theory, it is believed that red wine extract does have the potential to be effective versus hyperpigmentation and especially PIH (post-inflammatory hyperpigmentation) because of red wine's anti-inflammatory properties.

In some aspects, the topical solution composition exhibits the ability to reduce the appearance of excessive pigmentation, or "hyperpigmentation", and to lighten the appearance of human skin. The production of the topical solution is accomplished by providing a grape wine extract (also referred to herein as a grape extract) and adding vitamins that are capable of altering the pH of the topical solution composition within an aqueous solution with a carbomer base. The carbomer base acts as an emulsion stabilizer or "emulsifier."

In some aspects, the use of the topical solution composition disclosed herein reduces the appearance of hyperpigmentation by combining the extract of red wine grapes with one or more vitamins that function adjust the pH of the topical solution composition to an ideal level for maximum effect, without causing inflammation to the user's skin upon application.

Certain aspects of the present disclosure include a base formula of extract using a high concentration of magenta-colored red wine grapes that are fermented into wine via a controlled process, as specified herein above and in the '735 and 687' applications. Such extract of such fermented grapes is then combined with one or more vitamins, such as Panthenol (Vitamin B5) and/or Tocopherol Acetate (Vitamin E). In some such aspects, the vitamins are combined with the extract within a cold manufacturing process, in which the extract and vitamins are mixed at a temperature of ranging between 20 degrees Celsius and 40 degrees Celsius to compound a stable solution that maximizes the effects of a high concentration of resveratrol within the red wine extract. Panthenol and Tocopherol Acetate are used within the solution to adjust the pH level in order to maintain the solution's anti-oxidant effectiveness and stability.

In certain aspects, the pH of the topical solution composition ranges from 2.5 to 5.5, or from 3.0 to 5.0, or from 3.5 to 4.5, for example. As evidenced below, in Example 1, it has been found that when the pH of the topical solution composition is from 2.5 to 5.5, the topical solution composition is effective in reducing the visibility of pigmented lesions on skin without causing skin irritation. In some such aspects, the topical solution composition has a pH of from 2.5 to 5.5 and a content of red wine grape extract of from 1.0 to 50.0 weight percent. Without being bound by theory, it is believed that an otherwise identical topical solution composition having a pH of greater than 5.5 is not effective at reducing the visibility of pigmented lesions on skin without causing skin irritation, and that an otherwise identical topical solution composition having a pH of less than 2.5 causes skin irritation.

In some aspects, a topical solution composition in accordance with the present disclosure, having a pH of from 2.5 to 5.5 and a content of red wine grape extract of from 1.0 to 50.0 weight percent, is capable of reducing the number of visible lesions by from 10% to 50%, or from 15% to 40%, or from 20% to 35%, or from 25% to 30% (e.g., after a twice daily application of the topical solution composition onto the skin over a thirty-day period). For example, if a user applies the topical solution composition to an affected area having ten visible lesions, twice daily for thirty days, that user may experience a reduction in the number of visible lesions by from 10% to 50% (i.e., reducing the number of visible lesions from an original 10 visible lesions to a resulting number of visible lesions ranging from 9 to 5). One skilled in the art would understand that the number of visible lesions reduced by use of the present topical solution composition is not limited to these percentages.

Without being bound by theory, it is believed that the reduction of hyperpigmentation results from a combination of the anti-oxidant and anti-inflammatory properties of red wine grape extract and the composition having a pH ranging from 2.5 to 5.5. Healthy and normal human skin has a pH of approximately 7.0 or neutral pH. However, the outer layers of human skin within the stratum corneum and epidermal layer have a pH level of approximately 5.5 for normal, healthy skin. Thus, by having a pH adjusted to reside within the range of 2.5 to 5.5, the present composition is more effective in reducing lesions of pigmentation on the upper skin layers, as well as reducing visible inflammation. That the pH levels maintain a difference in performance is an observation unique to the present composition, as one skilled in the art would have no expectation of success in adjusting the pH level of a topical solution to enhance that solutions abilities to reduce hyperpigmentation. In fact, often solutions of known skin lighteners, such as hydroquinone, require functional pHs of 2.0 or lower to be deemed effective. Thus, the present composition surprisingly and unexpectedly exhibits skin lightening capability at a pH ranging from 2.5 to 5.5.

The content of red wine grape extract may range from 1.0 to 50.0 weight percent, or from 5 to 45 weight percent, or from 10 to 40 weight percent, or from 15 to 35 weight percent, or from 20 to 30 weight percent, based on a total weight of the topical solution composition. The use of the cold manufacturing process described herein, the use of a pH range of from 2.5 to 5.5, and the need to stabilize the red wine extract within the emulsion are each considered when determining the types and amounts of additives and additional ingredients included within the topical solution composition.

In some aspects, the topical solution composition is in the form of a gel. In other aspects, the topical solution composition is in the form of a cream.

Some aspects of the topical solution composition gel include ingredients, including but not limited to: deionized water, red wine extract, aloe barbendesis leaf juice, cucumber extract, hyaluronic acid, isoprene glycol, tocopherol acetate (Vitamin E), chamomile extract, jojoba oil, hydrolized silk protein, nettle extract, hydrolyzed wheat protein, phytic acid, wheat germ oil, horsetail extract, centella *asiatica* extract, *Chlorella vulgaris* extract, hydrolized align, butylene glycol, D-Panthenol (Vitamin B5), caffeine extract, carbomer, phenoxy ethanol, methylparaben, butylparaben, ethylparaben, propylparaben, triethanolamine, or combinations thereof. Some aspects of the topical solution composition gel include deionized water in an amount ranging from 51 to 95 weight percent, or from 60 to 90 weight percent, or from 65 to 85 weight percent, or 70.9 weight percent. Some aspects of the topical solution composition gel include red wine extract in an amount ranging from 1 to 50 weight percent, or from 2 to 20 weight percent, or from 3 to 10 weight percent, or 5 weight percent. Some aspects of the topical solution composition gel include aloe barbendesis leaf juice in an amount ranging from 1 to 10 weight percent, or from 2 to 8 weight percent, or from 2.5 to 5 weight percent, or 3 weight percent. Some aspects of the topical solution composition gel include cucumber extract, hyaluronic acid, isoprene glycol, tocopherol acetate (Vitamin E), chamomile extract, jojoba oil, hydrolized silk protein, each, if present, in an amount ranging from 1 to 10 weight percent, or from 1.5 to 8 weight percent, or from 2 to 5 weight percent, or 2 weight percent. Some aspects of the topical solution composition gel include nettle extract, hydrolyzed wheat protein, phytic acid, wheat germ oil, horsetail extract, centella *asiatica* extract, *Chlorella vulgaris* extract, hydrolized align, butylene glycol, D-Panthenol (Vitamin B5), caffeine extract, and carbomer, each, if present, in an amount ranging from 0.1 to 5 weight percent, or from 0.2 to 3 weight percent, or from 0.3 to 1 weight percent, or 0.5 weight percent. Some aspects of the topical solution composition gel include phenoxyethanol, methylparaben, butylparaben, ethylparaben, propylparaben, triethanolamine, each, if present, in an amount ranging from 0.01 to 1 weight percent, or from 0.02 to 0.5 weight percent, or from 0.09 to 0.3 weight percent, or 0.2 weight percent, or 0.1 weight percent. An exemplary gel composition, conducive to mixing via the cold manufacturing process when producing the topical solution composition, is set forth in the following Table, below.

TABLE

Red Wine Gel for reducing hyperpigmentation
Red Wine Gel for reducing hyperpigmentation

| Ingredients | Percentages by volume |
| --- | --- |
| Deionized Water | 70.9 |
| Red Wine Extract | 5.0 |
| *Aloe Barbendesis* Leaf Juice | 3.0 |
| Cucumber Extract | 2.0 |
| Hyaluronic Acid | 2.0 |
| Isoprene Glycol | 2.0 |
| Tocopherol Acetate (Vitamin E) | 2.0 |
| Chamomile Extract | 2.0 |
| Jojoba Oil | 2.0 |
| Hydrolized Silk Protein | 2.0 |
| Nettle Extract | 0.5 |
| Hydrolyzed Wheat Protein | 0.5 |
| Phytic Acid | 0.5 |
| Wheat Germ Oil | 0.5 |
| Horsetail Extract | 0.5 |
| *Centella Asiatica* Extract | 0.5 |
| *Chlorella Vulgaris* Extract | 0.5 |
| Hydrolized Algin | 0.5 |
| Butylene Glycol | 0.5 |
| D-Panthenol (Vitamin B5) | 0.5 |
| Caffeine Extract | 0.5 |
| Carbomer | 0.5 |
| Phenoxyethanol | 0.2 |
| Methylparaben | 0.2 |
| Butylparaben | 0.2 |
| Ethylparaben | 0.2 |
| Propylparaben | 0.2 |
| Triethanolamine | 0.1 |

Some aspects of the topical solution composition cream include ingredients, including but not limited to: deionized water, red wine extract, isoprene glycol, dimethicone, dimethylpolisiloxane, squalane, chinesis seed oil, tetrahexyldecyl ascorbate (Vitamin C), tocopherol acetate (Vitamin E), panthenol (Vitamin B5), cetyl alcohol, shea butter, bees wax, cetearyl glycoside, xanthan gum, carbomer, santalum album (sandalwood) extract, phellondendron amurence bark extract, hordeium distichon (barley) extract, phenoxyethanol, methylparaben, propylparaben, butylparaben, or combinations thereof. Some aspects of the topical solution composition cream include deionized water in an amount ranging from 40 to 95 weight percent, or from 50 to 80 weight percent, or from 55 to 70 weight percent, or 60 weight percent. Some aspects of the topical solution composition cream include red wine extract in an amount ranging from 1 to 50 weight percent, or from 2 to 20 weight percent, or from 3 to 10 weight percent, or 6 weight percent. Some aspects of the topical solution composition cream include isoprene glycol, dimethicone, dimethylpolisiloxane, or combinations thereof, each, if present, in an amount ranging from 1 to 10 weight percent, or from 1.5 to 8 weight percent, or from 2 to 5 weight percent, or 4 weight percent or 5 weight percent. Some aspects of the topical solution composition cream include squalane, Chinese seed oil, tetrahexyldecyl ascorbate (Vitamin C), tocopherol acetate (Vitamin E), panthenol (Vitamin B5), cetyl alcohol, shea butter, bees wax, cetearyl glycoside, xanthan gum, or combinations thereof, each, if present, in an amount ranging from 0.1 to 10 weight percent, or from 0.2 to 8 weight percent, or from 0.3 to 5 weight percent, or from 1 to 2 weight percent, or 1 weight percent, or 2 weight percent. Some aspects of the topical solution composition cream include carbomer, santalum album (sandalwood) extract, phellondendron amurence bark extract, hordeium distichon (barley) extract, phenoxyethanol, methylparaben, propylparaben, butylparaben, or combinations thereof, each, if present, in an amount ranging from 0.1 to 5 weight percent, or from 0.2 to 3 weight percent, or from 0.25 to 1 weight percent, or from 0.25 to 0.5 weight percent, or 0.5 weight percent, or 0.25 weight percent. An exemplary cream composition, conducive to mixing via the cold manufacturing process when producing the topical solution composition, is set forth in the following Table, below.

TABLE

Red Wine Cream for reducing hyperpigmentation
Red Wine Cream for reducing hyperpigmentation

| Ingredients | Percentages by volume |
|---|---|
| Deionized Water | 60.0 |
| Red Wine Extract | 6.0 |
| Isoprene Glycol | 5.0 |
| Dimethicone | 4.0 |
| Dimethylpolisiloxane | 4.0 |
| Squalane | 2.0 |
| Chinesis Seed Oil | 2.0 |
| Tetrahexyldecyl Ascorbate (Vitamin C) | 2.0 |
| Tocopherol Acetate (Vitamin E) | 2.0 |
| Panthenol (Vitamin B5) | 2.0 |
| Cetyl Alcohol | 2.0 |
| Shea Butter | 2.0 |
| Bees Wax | 2.0 |
| Cetearyl Glycoside | 1.0 |
| Xanthan Gum | 1.0 |
| Carbomer | 0.5 |
| Santalum Album (Sandalwood) Extract | 0.5 |
| Phellondendron Amurence Bark Extract | 0.5 |
| Hordeium Distichon (Barley) Extract | 0.5 |
| Phenoxyethanol | 0.25 |
| Methylparaben | 0.25 |
| Propylparaben | 0.25 |
| Butylparaben | 0.25 |

As is understood by those skilled in the art, different combinations of ingredients may be used without deviating from the scope of the present disclosure.

Example 1—Red Wine Lightning Laboratory Trial

A trial experiment was conducted to investigate a red wine gel formulation in accordance the formulation listed in the Table above (TABLE—Red Wine Gel for reducing hyperpigmentation).

Test Materials Used in Example 1

Unit A: Red wine & Vitamin B5 Gel at a 5 weight % concentration; with a pH of 5.5

Unit B: Red Wine & B5 Gel at a 5 weight % concentration; with a pH at 2.5

Unit C: Control gel consisting of Vitamin B5 but no red wine extract; with a pH at 7.0

Test Subjects

Six patients were included in the study:
1: 65 year old Asian female
2: 50 year old Asian female
3: 50 year old Asian female
4: 45 year old Caucasian male
5: 25 year old Hispanic male
6: 25 year old Asian male All subjects at the time of the testing were of generally good health.

Study Methodology

The subjects (i.e., six patients) were each given a 30 ml bottle of a gel formulation that was marked A, B or C, corresponding to Units A, B, and C. Thus, each bottle corresponded to one of the test materials. The subjects were instructed to wash their face and then apply the gel twice daily: once in the morning and once before going to sleep. The amount applied to the face was 0.3 grams per dose (per application). The study was conducted for 30 days.

Results of Study

The study was judged based on the attained reduction of visible pigmentation lesions by area, by visual assessment from Day 1 of the study before the first application of gel, to the Day 30 of the study, after the final application of gel. The results are presented in the Table below.

TABLE

Example 1 Study Results

| Subject | Gel Used | Result Day 1 | Result Day 30 |
|---|---|---|---|
| 1 | B | — | 50% reduction in visible pigmentation lesions |
| 2 | B | — | 45% reduction in visible pigmentation lesions |
| 3 | A | — | 10% reduction in visible pigmentation lesions |
| 4 | C | — | 0% reduction in visible pigmentation lesions |
| 5 | C | — | 3% reduction in visible pigmentation lesions |
| 6 | A | — | 18% reduction in visible pigmentation lesions |

The percentage in the Table is the amount of area of pigmented lesions reduced on the face. This was done as a self-assessment by the subject, and also by an observer to determine the amount of reduced lesions.

CONCLUSIONS

This study was able to observe that there was a noticeably visible result from application of gels with Red Wine Extract on reducing pigmented lesions, and that this result was especially apparent on gels with a lower pH than 7.0. Compared to the control gel, both of the red wine gels were able to display visible results.

It was found however that when the pH of the gel was narrowed to between 2.5 and 5.5, and not exceeding 5.5, and when the concentrations of the red wine extract were between 1.0% and 50.0%, that the resulting gel was observed as being effective in reducing the visibility of pigmented lesions on skin that it was applied to. Topical solutions employing red wine extract that had a pH above 5.5 were found not to be effective in reducing hyperpigmented lesions on skin, while solutions that were below 2.5 were found to be highly inflammatory on skin to the point of ineffectiveness.

It should be noted and understood that many of the specific features or combination of features illustrated in or introduced above (or described in the claims submitted below), and\or discussed in accompanying descriptions, may be combined with or incorporated with or other feature(s) described or illustrated in any other Figure provided herein. Moreover, the following claims serve also to describe and illustrate some (but not all) aspects of the present disclosure. The claims serve therefore as an integral part of the present disclosure.

The foregoing description has been presented for purposes of illustration and description of preferred aspects. This description is not intended to limit associated concepts to the various compositions, processes, and methods specifically described herein. For example, aspects of the processes and compositions illustrated by the Figures and discussed above may be employed or prove suitable for use with methods and compositions. The aspects described and illustrated herein are further intended to explain the best modes for practicing the compositions and methods, and to enable others skilled in the art to utilize same and other aspects and with various modifications required by the particular applications or uses of the present disclosure.

What is claimed is:

1. A topical solution composition comprising:
   a red wine extract present in an amount ranging from 1.0 to 50.0 weight percent based on a total weight of the topical solution composition, the red wine extract comprising resveratrol;
   water;
   an emulsifier;
   vitamins, wherein the vitamins are present in the topical solution composition in an amount that is sufficient to provide the topical solution composition with a pH ranging from 2.5 to 4.5;
   wherein the topical solution composition is in the form of a topical gel or a topical cream; and
   wherein the topical solution composition exhibits the capability of reducing the number of visible lesions on human skin by from 10% to 50%.

2. The topical solution composition of claim 1, wherein the resveratrol comprises cis- and trans-resveratrol.

3. The topical solution composition of claim 1, wherein the emulsifier includes a carbomer base.

4. The topical solution composition of claim 1, wherein the red wine extract has an amount of alcohol of no more than 2 percent by volume.

5. The topical solution composition of claim 1, wherein the topical solution composition includes Tocopherol Acetate (Vitamin E), Panthenol (Vitamin B5), or combinations thereof.

6. The topical solution composition of claim 1, wherein the red wine extract is extracted from magenta-colored red wine grapes.

7. The topical solution composition of claim 1, wherein the topical solution composition exhibits the capability of reducing the number of visible lesions on human skin by from 15% to 40%.

8. The topical solution composition of claim 1, wherein the topical solution composition is in the form of the topical gel.

9. The topical solution composition of claim 8, wherein the topical solution composition includes: deionized water, red wine extract, aloe barbendesis leaf juice, cucumber extract, hyaluronic acid, isoprene glycol, tocopherol acetate (Vitamin E), chamomile extract, jojoba oil, hydrolyzed silk protein, nettle extract, hydrolyzed wheat protein, phytic acid, wheat germ oil, horsetail extract, centella *asiatica* extract, *chlorella* vulgaris extract, hydrolyzed align, butylene glycol, D-Panthenol (Vitamin B5), caffeine extract, carbomer, phenoxyethanol, methylparaben, butylparaben, ethylparaben, propylparaben, triethanolamine, or combinations thereof.

10. The topical solution composition of claim 1, wherein the topical solution composition is in the form of the topical cream.

11. The topical solution composition of claim 10, wherein the topical solution composition includes: deionized water, red wine extract, isoprene glycol, dimethicone, dimethylpolysiloxane, squalane, chinesis seed oil, tetrahexyldecyl ascorbate (Vitamin C), tocopherol acetate (Vitamin E), panthenol (Vitamin B5), cetyl alcohol, shea butter, bees wax, cetearyl glycoside, xanthan gum, carbomer, santalum album (sandalwood) extract, phellodendron *amurense* bark extract, *hordeum* distichon (barley) extract, phenoxyethanol, methylparaben, propylparaben, butylparaben, or combinations thereof.

12. The topical solution composition of claim 1, wherein the topical solution composition is in the form of the topical gel or the topical cream for revitalizing damaged skin;
   wherein the red wine extract is an extract of fermented grapes having concentrations of resveratrol;
   the topical solution composition further comprising vitamins, including vitamin B5 or vitamin E.

13. The topical solution composition of claim 12, comprising both vitamin B5 and vitamin E.

14. The topical solution composition of claim 12, wherein the grapes are of a magenta color.

15. The topical solution composition of claim 12, wherein the pH is between 2.5 and 4.0.

16. The topical solution composition of claim 12, wherein the topical solution composition includes Carbomer, Isoprene Glycol, Xanthan Gum, Butylene Glycol, or combinations thereof; and wherein the topical solution composition is in the form of a gel.

17. The topical solution of claim 12, wherein the topical solution composition includes Isoprene Glycol, Polyglyceryl-2 Stearate, Dimethylpolysiloxane Cetyl Alcohol, Bees Wax, Cetearyl Glucoside, Xanthan Gum, Carbomer, or combinations thereof; and wherein the topical solution composition is in the form of a cream.

18. The topical solution composition of claim 12, wherein the red wine extract is extracted from grapes that are merlot; cabernet; or combinations thereof.

19. The topical solution composition of claim 4, wherein the red wine extract is an extract from grapes fermented by use of yeast as an agent for a duration of between seven days and forty-five days, at a temperature between 35 degrees F. and 95 degrees F., and at a humidity between 30 percent and 80 percent, wherein the amount of alcohol in the grape extract is not more than two percent by volume, whereby the grape extract is in powder form.

20. The topical solution composition of claim 19, wherein the red wine extract is an extract from grapes fermented to yield a product having an alcohol level no more than 2% by volume and such that resveratrol is produced from Coumaroyl CoA molecule with three Coumaroyl CoA molecules in three successive reduction reactions yielding a long chain molecule followed by a cylcization process by resveratrol synthase yielding said resveratrol.

21. The topical solution composition of claim 1,
wherein the red wine extract is extracted from fermented grapes having a concentration of resveratrol;
wherein the emulsifier includes a carbomer base;
wherein the topical solution composition has a pH within a range of 2.5 to 3.5; and
wherein the topical solution composition includes vitamins selected from the group of vitamins consisting of: B5; vitamin E; and combinations thereof.

22. The topical solution composition of claim 21, wherein the red wine extract is present in an amount ranging from 5 to 45 weight percent based on a total weight of the of the topical solution composition.

23. The topical solution composition of claim 21, wherein the topical solution composition exhibits the capability of reducing the number of visible hyperpigmentation lesions on human skin by from 20% to 35%.

24. A topical solution cream or gel comprising:
a red wine extract present in an amount ranging from 1.0 to 50.0 weight percent based on a total weight of the of the topical solution composition, the red wine extract comprising resveratrol, wherein the red wine extract has an amount of alcohol of no more than 2 percent by volume; and
water;
an emulsifier;
vitamins, wherein the vitamins are present in the topical solution cream or gel in an amount that is sufficient to provide the topical solution cream or gel with a pH ranging from 2.5 to 3.5;
wherein the topical solution cream or gel exhibits the capability of reducing the number of visible lesions on human skin by from 10% to 50%.

25. A topical solution gel comprising:
a red wine extract present in an amount ranging from 1.0 to 50.0 weight percent based on a total weight of the of the topical solution composition, the red wine extract comprising resveratrol, wherein the red wine extract has an amount of alcohol of no more than 2 percent by volume;
water;
an emulsifier; and
vitamins including vitamin B5, wherein the vitamins are present in the topical solution gel in an amount that is sufficient to provide the topical solution gel with a pH ranging from 2.5 to 5.5;
wherein the topical solution gel exhibits the capability of reducing the number of visible lesions on human skin by from 10% to 50%.

26. The topical solution composition of claim 1, wherein the vitamins are present in the topical solution composition in an amount that is sufficient to provide the topical solution composition with a pH ranging from 2.5 to 3.5.

27. The topical solution composition of claim 1, wherein the vitamins are present in the topical solution composition in an amount that is sufficient to provide the topical solution composition with a pH ranging from 2.5 to 3.0.

* * * * *